(12) United States Patent
Amos et al.

(10) Patent No.: US 7,435,700 B2
(45) Date of Patent: Oct. 14, 2008

(54) CHROMIUM OXIDE COMPOSITIONS CONTAINING ZINC, THEIR PREPARATION AND THEIR USE AS CATALYSTS AND CATALYST PRECURSORS

(75) Inventors: Tammy Georgette Amos, Hockessin, DE (US); Velliyur Nott Mallikarjuna Rao, Wilmington, DE (US); Allen Capron Sievert, Elkton, MD (US); Shekhar Subramoney, Hockessin, DE (US)

(73) Assignee: E.I. du Pont de Nemars and Company, Wilmington, DE (US)

(*) Notice: Subject to any disclaimer, the term of this patent is extended or adjusted under 35 U.S.C. 154(b) by 0 days.

(21) Appl. No.: 10/572,628

(22) PCT Filed: Oct. 13, 2004

(86) PCT No.: PCT/US2004/034446

§ 371 (c)(1),
(2), (4) Date: Mar. 17, 2006

(87) PCT Pub. No.: WO2005/037431

PCT Pub. Date: Apr. 28, 2005

(65) Prior Publication Data

US 2007/0004585 A1    Jan. 4, 2007

Related U.S. Application Data

(60) Provisional application No. 60/511,353, filed on Oct. 14, 2003.

(51) Int. Cl.
*B01J 21/00* (2006.01)
*C07C 17/00* (2006.01)

(52) U.S. Cl. .................. 502/100; 570/154
(58) Field of Classification Search .......... 570/163; 502/318; 549/266; 554/124
See application file for complete search history.

(56) References Cited

U.S. PATENT DOCUMENTS

| | | | | |
|---|---|---|---|---|
| 2,178,761 A | * | 11/1939 | Lazier | 568/485 |
| 2,401,850 A | * | 6/1946 | Whitman | 570/154 |
| 3,027,316 A | * | 3/1962 | Ryer et al. | 208/134 |
| 3,878,257 A | | 4/1975 | Bruce, Jr. | |
| 5,281,568 A | | 1/1994 | Scott et al. | |
| 5,345,017 A | | 9/1994 | Rao et al. | |
| 5,449,656 A | | 9/1995 | Scott et al. | |
| 5,623,092 A | | 4/1997 | Scott et al. | |
| 5,763,698 A | | 6/1998 | Manzer et al. | |
| 6,403,524 B2 | | 6/2002 | Scott et al. | |
| 2001/0011061 A1 | | 8/2001 | Scott et al. | |

FOREIGN PATENT DOCUMENTS

| | | | |
|---|---|---|---|
| AU | A-80340/94 | | 6/1995 |
| DE | 2358254 | * | 6/1975 |
| DE | 2358254 A | * | 6/1975 |
| EP | 0 641 598 | | 3/1995 |
| EP | 0 957 074 | | 11/1999 |
| EP | 1 038 858 | | 9/2000 |
| GB | 1 225 324 | | 3/1971 |
| GB | 2275924 | * | 9/1994 |
| GB | 2275924 A | * | 9/1994 |
| WO | WO2005/037742 | | 4/2005 |
| WO | WO2005/037743 | | 4/2005 |
| WO | WO2005/037744 | | 4/2005 |

OTHER PUBLICATIONS

U.S. Appl. No. 10/572,626, filed Oct. 13, 2004, Rao et al.
U.S. Appl. No. 10/572,627, filed Oct. 13, 2004, Rao et al.
U.S. Appl. No. 10/572,625, filed Oct. 13, 2004, Rao et al.

* cited by examiner

*Primary Examiner*—Janet L. Andres
*Assistant Examiner*—MLouisa Lao

(57) ABSTRACT

A chromium-containing catalyst is disclosed which includes both $ZnCr_2O_4$ and crystalline α-chromium oxide. The $ZnCr_2O_4$ contains between about 10 atom percent and 67 atom percent of the chromium in the composition and at least about 70 atom percent of the zinc in the composition, and at least about 90 atom percent of the chromium present as chromium oxide in the composition is present as $ZnCr_2O_4$ or crystalline α-chromium oxide. Also disclosed are a method for preparing this composition comprising $ZnCr_2O_4$ and crystalline α-chromium oxide; and a chromium-containing catalyst composition prepared by treatment of the composition comprising $ZnCr_2O_4$ and crystalline α-chromium oxide with a fluorinating agent. Also disclosed is a process for changing the fluorine distribution in a halogenated hydrocarbon, or incorporating fluorine in a saturated or unsaturated hydrocarbon, in the presence of at least one composition selected from the group consisting of (i) the $ZnCr_2O_4$ and crystalline α-chromium oxide compositions and (ii) the $ZnCr_2O_4$ and crystalline α-chromium oxide compositions which have been treated with a fluorinating agent.

16 Claims, 2 Drawing Sheets

CHROMIUM OXIDE COMPOSITIONS CONTAINING ZINC, THEIR PREPARATION AND THEIR USE AS CATALYSTS AND CATALYST PRECURSORS

This application represents a national filing under 35 U.S.C. 371 of PCT International Application No. PCT/US2004/034446 filed Oct. 13, 2004, and claims priority benefit of U.S. application Ser. No. 60/511,353 filed Oct. 14, 2003.

FIELD OF THE INVENTION

This invention relates to chromium-containing compositions, their preparation, and their use for the catalytic processing of hydrocarbons and/or halogenated hydrocarbons.

BACKGROUND

U.S. Pat. No. 5,281,568 discloses a fluorination catalyst containing chromium and zinc. The amount of zinc may be in the range of from about 0.5% by weight to about 25% by weight.

Australian Patent Document No. AU-A-80340/94 discloses bulk or supported catalysts based on chromium oxide (or oxides of chromium) and at least one other catalytically active metal (e.g., Mg, V, Mn, Fe, Co, Ni, or Zn), in which the major part of the oxide(s) is in the crystalline state (and when the catalyst is a bulk catalyst, its specific surface, after activation with HF, is at least 8 m$^2$/g). The crystalline phases disclosed include $Cr_2O_3$, $CrO_2$, $NiCrO_3$, $NiCrO_4$, $NiCr_2O_4$, $MgCrO_4$, $ZnCr_2O_4$ and mixtures of these oxides.

U.S. Pat. No. 3,878,257 discloses the catalyzed reaction of 1,1,2-trichlorotrifluoropropene with hydrogen fluoride to form 2-chloropentafluoropropene in the presence of a catalyst combination of activated anhydrous chromium(III) oxide and a divalent zinc compound.

There remains a need for catalysts that can be used for processes such as the selective fluorination and chlorofluorination of saturated and unsaturated hydrocarbons, hydrochlorocarbons, hydrochlorofluorocarbons, and chlorofluorocarbons, the fluorination of unsaturated fluorocarbons, the isomerization and disproportionation of fluorinated organic compounds, the dehydrofluorination of hydrofluorocarbons, and the chlorodefluorination of fluorocarbons.

SUMMARY OF THE INVENTION

This invention provides a chromium-containing catalyst composition comprising $ZnCr_2O_4$ (zinc chromite) and crystalline α-chromium oxide wherein the $ZnCr_2O_4$ contains between about 10 atom percent and 67 atom percent of the chromium in the composition and at least about 70 atom percent of the zinc in the composition, and wherein at least about 90 atom percent of the chromium present as chromium oxide in the composition is present as $ZnCr_2O_4$ or crystalline α-chromium oxide.

This invention also provides a method for preparing said composition comprising $ZnCr_2O_4$ and crystalline α-chromium oxide. The method comprises (a) co-precipitating a solid by adding ammonium hydroxide (aqueous ammonia) to an aqueous solution of a soluble zinc salt and a soluble trivalent chromium salt that contains at least three moles of nitrate (i.e., $NO_3^-$) per mole of chromium (i.e., $Cr^{3+}$) in the solution and has a zinc concentration of from about 5 mole % to about 25 mole % of the total concentration of zinc and chromium in the solution and where at least three moles of ammonium (i.e., $NH_4^+$) per mole of chromium (i.e., $Cr^{3+}$) in the solution has been added to the solution, (b) collecting the co-precipitated solid formed in (a); (c) drying the collected solid; and (d) calcining the dried solid.

This invention also provides a chromium-containing catalyst composition, said composition being prepared by treatment of said composition comprising $ZnCr_2O_4$ and crystalline α-chromium oxide with a fluorinating agent (e.g., anhydrous hydrogen fluoride).

This invention also provides a process for changing the fluorine distribution (i.e., content and/or arrangement) in a halogenated hydrocarbon, or incorporating fluorine in a saturated or unsaturated hydrocarbon, in the presence of a catalyst. The process is characterized by using as a catalyst at least one composition selected from the group consisting of (i) the $ZnCr_2O_4$ and crystalline α-chromium oxide compositions of this invention and (ii) the $ZnCr_2O_4$ and crystalline α-chromium oxide compositions of this invention which have been treated with a fluorinating agent.

DETAILED DESCRIPTION

Figure 1:
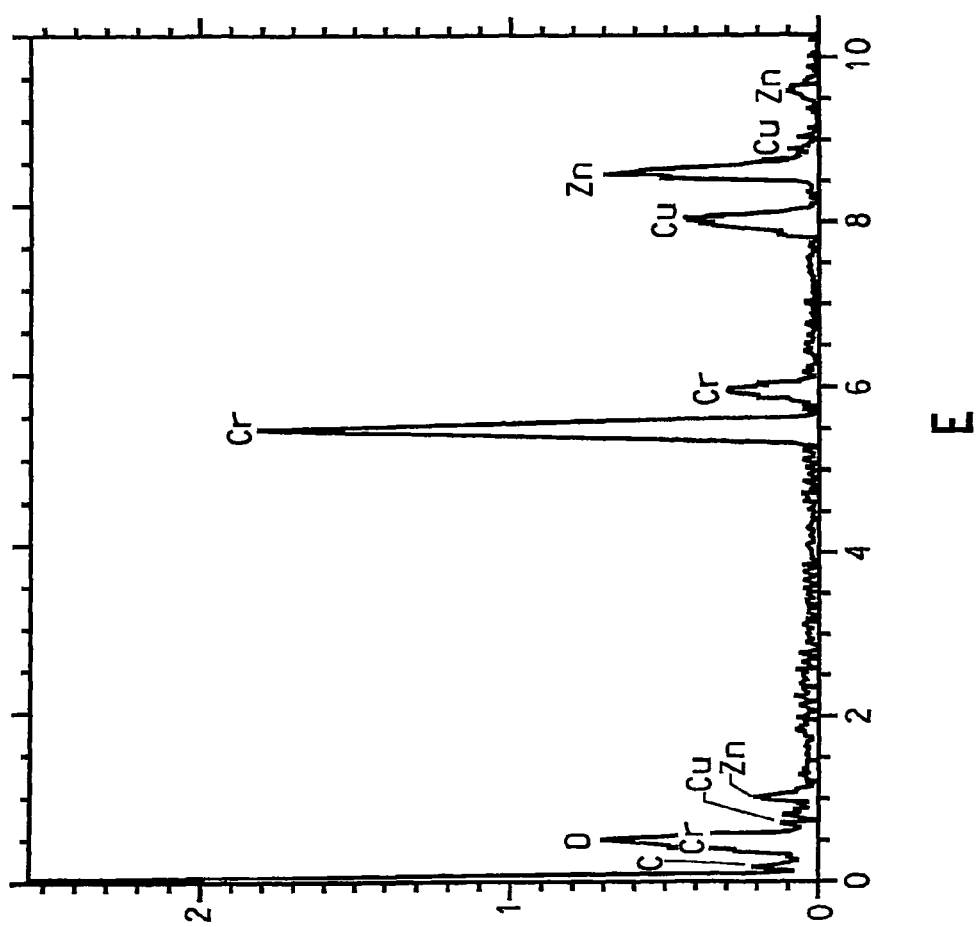
FIG. 1 represents an energy dispersive spectroscopy spectrum of the zinc chromite phase present in a zinc/chromium oxide composition nominally containing 20 atom % zinc.

The compositions of this invention are zinc- and chromium-containing oxides comprising $ZnCr_2O_4$ and crystalline α-chromium oxide wherein the $ZnCr_2O_4$ contains between about 10 atom percent and 67 atom percent of the chromium in the composition and at least about 70 atom percent of the zinc in the composition. The compositions disclosed include a catalytic composition comprising $ZnCr_2O_4$ and crystalline α-chromium oxide.

The compositions of this invention may be prepared by the method described above using co-precipitation followed by calcination. Such methods include, but are not limited to, precipitation from aqueous solutions containing chromium and zinc salts in the desired molar ratio.

In a typical co-precipitation technique, an aqueous solution of zinc and chromium(III) salts is prepared. The relative concentrations of the zinc and chromium(III) salts in the aqueous solution is dictated by the bulk atom percent zinc relative to chromium desired in the final catalyst. The concentration of zinc is from about 5 mole % to about 25 mole % of the total concentration of zinc and chromium in the solution. The concentration of chromium(III) in the aqueous solution is typically in the range of 0.3 to 3 moles per liter with 0.75-1.5 moles per liter being a preferred concentration. While different chromium(III) salts might be employed, chromium(III) nitrate or its hydrated forms such as $[Cr(NO_3)_3(H_2O)_9]$, are the most preferred chromium(III) salts for preparation of said aqueous solution.

While different zinc salts might be employed for preparation of said aqueous solutions, preferred zinc salts for preparation of catalysts for the process of this invention include zinc(II) nitrate and its hydrated forms such as $[Zn(NO_3)_2(H_2O)_6]$.

The aqueous solution of the chromium(III) and zinc salts may then be evaporated either under vacuum or at elevated temperature to give a solid which is then calcined.

It is preferred to treat the aqueous solution of the chromium (III) and zinc salts with a base such as ammonium hydroxide (aqueous ammonia) to precipitate the zinc and chromium as the hydroxides. Bases containing alkali metals such as sodium or potassium hydroxide or the carbonates may be used but are not preferred. The addition of ammonium hydroxide to the aqueous solution of the chromium(III) and zinc salts is typically carded out gradually over a period of 1 to 12 hours. The pH of the solution is monitored during the addition of base. The final pH is typically in the range of 6.0 to 11.0, preferably from about 7.5 to about 9.0, most preferably about 8.0 to 8.7. The precipitation of the zinc and chromium hydroxide mixture is typically carried out at a temperature of about 15° C. to about 60° C., preferably from about 20° C. to about 40° C. After the ammonium hydroxide is added, the mixture is typically stirred for up to 24 hours. The precipitated chromium and zinc hydroxides serve as precursors to $ZnCr_2O_4$ and crystalline α-chromium oxide.

After the precipitation of the zinc and chromium hydroxide mixture is complete, the mixture is dried. This may be carried out by evaporation in an open pan on a hot plate or steam bath or in an oven or furnace at a suitable temperature. Suitable temperatures include temperatures from about 60° C. to about 130° C. (e.g., from about 100° C. to about 120° C.). Alternatively the drying step may be carried out under vacuum using, for example, a rotary evaporator.

Optionally, the precipitated zinc and chromium hydroxide mixture may be collected and, if desired, washed with deionized water before drying. Preferably the precipitated zinc and chromium hydroxide mixture is not washed prior to the drying step.

After the zinc and chromium hydroxide mixture has been dried, the nitrate salts are then decomposed by heating the solid from about 250° C. to about 350° C. The resulting solid is then calcined at temperatures of from about 400° C. to about 1000° C., preferably from about 400° C. to about 900° C. The calcination may be carried out in a crucible or pan in an oven or furnace or in a tubular reactor. The calcination temperature can influence the activity of the catalysts and the product distribution. Lower calcination temperatures (i.e., those below about 500° C.) may result in the presence of some residual nitrate impurities. The calcination is preferably carried out in the presence of oxygen, most preferably in the presence of air.

Of note are compositions comprising $ZnCr_2O_4$ and crystalline α-chromium oxide wherein the $ZnCr_2O_4$ is formed during the calcination step.

Of note are chromium-containing catalyst compositions of this invention which comprise $ZnCr_2O_4$ (zinc chromite) and crystalline α-chromium oxide wherein the $ZnCr_2O_4$ contains between about 20 atom percent and about 50 atom percent of the chromium in the composition. Also of note are chromium-containing catalyst compositions of this invention which comprise $ZnCr_2O_4$ (zinc chromite) and crystalline α-chromium oxide wherein the $ZnCr_2O_4$ contains at least about 90 atom percent of the zinc in the composition. Also of note are chromium-containing catalyst compositions of this invention comprising zinc chromite and crystalline α-chromium oxide wherein greater than 95 atom percent of the chromium that is not present as zinc chromite is present as crystalline α-chromium oxide. Also of note are chromium-containing catalyst compositions of this invention which consist essentially of $ZnCr_2O_4$ (zinc chromite) and crystalline α-chromium oxide.

The compositions of this invention may be characterized by well-established analytical techniques including transmission electron microscopy (TEM), energy dispersive spectroscopy (EDS) and X-ray diffraction. EDS is an analytical tool available in conjunction with scanning or analytical TEM.

Figure 2:
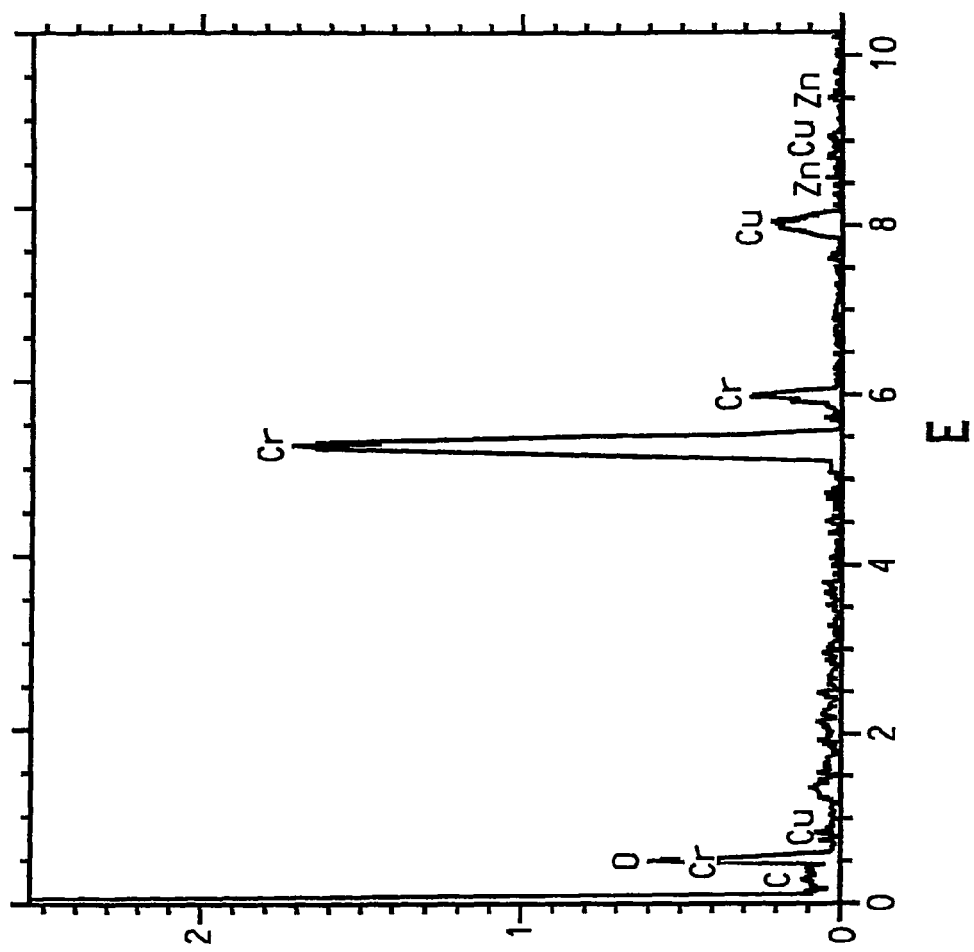
FIG. 2 represents an energy dispersive spectroscopy spectrum of the α-$Cr_2O_3$ phase present in the same zinc/chromium oxide composition nominally containing 20 atom % zinc

The presence of zinc in the various zinc and chromium oxide compositions of this invention is clearly indicated by elemental analysis using EDS. EDS analyses of various Cr/Zn oxide samples having a Zn content of 2, 5, 10, and 20 atom % calcined at 900° C. indicate the presence of two phases: a zinc chromite phase where the relative content of Cr to Zn is 2 to 1 and a chromium oxide phase with no evidence of zinc in the lattice (Zn is not detected in the EDS spectrum of this phase). For example, FIG. 1 shows the EDS spectrum of the zinc chromite phase present in a zinc/chromium composition nominally containing 20 atom % zinc. For comparison, FIG. 2 shows the EDS spectrum of the α-$Cr_2O_3$ phase present in the same zinc/chromium composition nominally containing 20 atom % zinc. In each of these Figures, X-ray intensity, I, representing thousands of counts is plotted against energy level, E, representing thousands of electron volts (keV). Peaks in each plot correlate with the presence of certain elements. Calibration experiments have shown that the relative heights of the Ka peaks for the metals in mixed zinc and chromium oxide compositions reflect the mole ratio of zinc and chromium in the compositions. Thus, the EDS spectra are valid on a quantitative basis for elements whose atomic masses are fairly similar. These results are also consistent with wide-angle X-ray diffraction analysis experiments of the various samples, which indicated that each sample consisted of two phases: a pure α-$Cr_2O_3$ and a $ZnCr_2O_4$ spinel phase. There are no significant changes in the cell volume of the $Cr_2O_3$ phase in the Cr/Zn samples compared to zinc-free chromium oxide. This indicates that there is no detectable substitution of Zn in the $Cr_2O_3$ lattice. The weight percent of the $ZnCr_2O_4$ phase increases with increasing zinc concentration.

The compositions of this invention may further comprise one or more additives in the form of metal compounds that can alter the selectivity and/or activity of the catalyst compositions containing crystalline α-$Cr_2O_3$ and $ZnCr_2O_4$ or fluorinated α-$Cr_2O_3$ and $ZnCr_2O_4$. Suitable additives may be selected from the group consisting of fluorides, oxides, or oxyfluoride compounds of Mg, Ca, Zn, Sc, Y, La, Ti, Zr, Hf, V, Nb, Ta, Mo, W, Mn, Re, Fe, Ru, Co, Rh, Ir, Ni, Pd, Pt, Cu, Ag, Au, and Ce, The total content of the additive(s) in the compositions of the present invention may be from about 0.05 atom % to about 15 atom % based on the total metal content of the compositions provided that when the additive is a compound of zinc, the additive comprises less than 30 mole percent of the total zinc in the final composition. The additives may be incorporated into the compositions of the present invention by standard procedures such as impregnation of a solution of the additive followed by drying or co-precipitation.

The calcined zinc chromite/α-chromium oxide compositions of the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process of the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

As noted above catalysts provided in accordance with this invention may be used for changing the fluorine distribution and/or content of halogenated hydrocarbons. The catalysts of this invention may also be used to incorporate fluorine into a saturated or unsaturated hydrocarbon. Processes for changing the fluorine distribution in halogenated hydrocarbons include fluorination, chlorofluorination, isomerization, disproportionation, dehydrofluorination and chlorodefluorination. Processes for incorporating fluorine into saturated or unsaturated hydrocarbons include chlorofluorination of saturated or unsaturated hydrocarbons and fluorination of unsaturated hydrocarbons. The processes of this invention are characterized by using as a catalyst at least one composition selected from the group consisting of the $ZnCr_2O_4$/α-chromium oxide compositions of this invention and the $ZnCr_2O_4$/α-chromium oxide compositions of this invention which have been treated with a fluorinating agent. Of note are processes wherein the fluorine content of a halogenated hydrocarbon compound or an unsaturated hydrocarbon compound is increased by reacting said compound with hydrogen fluoride in the vapor phase in the presence of said catalyst composition. Also of note are processes wherein the fluorine content of a halogenated hydrocarbon compound or a hydrocarbon compound is increased by reacting said compound with HF and $Cl_2$ in the vapor phase in the presence of said catalyst composition. Also of note are processes wherein the fluorine distribution in a halogenated hydrocarbon compound is changed by isomerizing said halogenated hydrocarbon compound in the presence of said catalyst composition. Also of note are processes wherein the fluorine distribution in a halogenated hydrocarbon compound is changed by disproportionating said halogenated hydrocarbon compound in the vapor phase in the presence of said catalyst composition. Also of note are processes wherein the fluorine content of a halogenated hydrocarbon compound is decreased by dehydrofluorinating said halogenated hydrocarbon compound in the presence of said catalyst composition. Also of note are processes wherein the fluorine content of a halogenated hydrocarbon compound is decreased by reacting said halogenated hydrocarbon compound with hydrogen chloride in the vapor phase in the presence of said catalyst composition.

Typical of saturated halogenated hydrocarbons suitable for fluorination, chlorofluorination, isomerization, disproportionation, dehydrofluorination and chlorodefluorination processes are those which have the formula $C_nH_aBr_bCl_cF_d$, wherein n is an integer from 1 to 6, a is an integer from 0 to 12, b is an integer from 0 to 4, c is an integer from 0 to 13, d is an integer from 0 to 13, the sum of b, c and d is at least 1 and the sum of a, b, c, and d is equal to 2n+2, provided that n is at least 2 for isomerization, disproportionation and dehydrofluorination processes, a is at least one for dehydrofluorination processes, b is 0 for chlorodefluorination processes, b+c is at least 1 for fluorination processes and is 0 for dehydrofluorination processes, a+b+c is at least 1 for fluorination, chlorofluorination, isomerization, disproportionation and dehydrofluorination processes and d is at least 1 for isomerization, disproportionation, dehydrofluorination and chlorodefluorination processes. Typical of saturated hydrocarbon compounds suitable for chlorofluorination are those which have the formula $C_qH_r$ where q is an integer from 1 to 6 and r is 2q+2. Typical of unsaturated halogenated hydrocarbons suitable for fluorination, chlorofluorination, isomerization, disproportionation, and chlorodefluorination processes are those which have the formula $C_pH_eBr_fCl_gF_h$, wherein p is an integer from 2 to 6, e is an integer from 0 to 10, f is an integer from 0 to 2, g is an integer from 0 to 12, h is an integer from 0 to 11, the sum of f, g and h is at least 1 and the sum of e, f, g, and h is equal to 2p, provided that f is 0 for chlorodefluorination processes, e+f+g is at least 1 for isomerization and disproportionation processes and h is at least 1 for isomerization, disproportionation and chlorodefluorination processes. Typical of saturated hydrocarbons suitable for chlorofluorination are those which have the formula $C_qH_r$ where q is an integer from 1 to 6 and r is 2q+2. Typical of unsaturated hydrocarbons suitable for fluorination and chlorofluorination are those which have the formula $C_iH_j$ where i is an integer from 2 to 6 and j is 2i.

The fluorination and chlorofluorination processes are typically conducted in the vapor phase in a tubular reactor at temperatures of from about 150° C. to 500° C. For saturated compounds the fluorination is preferably carried out from about 175° C. to 400° C. and more preferably from about 200° C. to about 350° C. For unsaturated compounds the fluorination is preferably carried out from about 150° C. to 350° C. and more preferably from about 175° C. to about 300° C. The reactions are typically conducted at atmospheric and superatmospheric pressures. For reasons of convenience in downstream separations processes (e.g., distillation), pressures of up to about 30 atmospheres may be employed. The contact time in the reactor is typically from about 1 to about 120 seconds and preferably from about 5 to about 60 seconds.

The amount of HF reacted with the unsaturated hydrocarbons or halogenated hydrocarbon compounds should be at least a stoichiometric amount. The stoichiometric amount is based on the number of Br and/or Cl substituents to be replaced by F in addition to one mole of HF to saturate the carbon-carbon double bond if present. Typically, the molar ratio of HF to the said compounds of the formulas $C_nH_aBr_bCl_cF_d$, $C_pH_eBr_fCl_gF_h$, and $C_iH_j$ can range from about 0.5:1 to about 100:1, preferably from about 2:1 to about 50:1, and more preferably from about 3:1 to about 20:1. In general, with a given catalyst composition, the higher the temperature and the longer the contact time, the greater is the conversion to fluorinated products. The above variables can be balanced, one against the other, so that the formation of higher fluorine substituted products is maximized.

Examples of saturated compounds of the formula $C_nH_aBr_bCl_cF_d$ which may be reacted with HF in the presence of the catalyst of this invention include $CH_2Cl_2$, $CH_2Br_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_6$, $C_3H_2BrCl_5$; $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3Cl_3F_2$, $C_3H_3Cl_2F_3$, $C_3H_3ClF_4$, $C_3H_4Cl_4$, $C_4Cl_4Cl_4$, $C_4Cl_4Cl_6$, $C_4H_5Cl_5$, $C_4H_5Cl_4F$, and $C_5H_4Cl_8$.

Specific examples of fluorination reactions of saturated halogenated hydrocarbon compounds which may be carried out under the conditions described above using the catalysts of this invention include the conversion of $CH_2Cl_2$ to $CH_2F_2$, the conversion of $CHCl_3$ to a mixture of $CHCl_2F$, $CHClF_2$, and $CHF_3$, the conversion of $CH_3CHCl_2$ to a mixture of $CH_3CHClF$ and $CH_3CHF_2$, the conversion of $CH_2ClCH_2Cl$ to a mixture of $CH_3CHClF$ and $CH_3CHF_2$, the conversion of $CH_3CCl_3$ to a mixture of $CH_3CCl_2F$, $CH_3CClF_2$, and $CH_3CF_3$, the conversion of $CH_2ClCF_3$ to $CH_2FCF_3$, the conversion of $CHCl_2CF_3$ to a mixture of $CHClFCF_3$ and $CHF_2CF_3$, the conversion of $CHClFCF_3$ to $CHF_2CF_3$, the conversion of $CHBrFCF_3$ to $CHF_2CF_3$, the conversion of $CCl_3CF_2CCl_3$ to a mixture of $CCl_2FCF_2CClF_2$ and $CClF_2CF_2CClF_2$, the conversion of $CCl_3CH_2CCl_3$ to $CF_3CH_2CF_3$ or a mixture of $CF_3CH_2CClF_2$ and $CF_3CH_2CF_3$, the conversion of $CCl_3CH_2CHCl_2$ to a mixture of $CF_3CH_2CHF_2$, $CF_3CH=CHCl$, and $CF_3CH=CHF$, the conversion of $CF_3CCl_2CClF_2$ to a mixture of $CF_3CCl_2CF_3$, and $CF_3CClFCF_3$, the conversion of $CF_3CCl_2CF_3$ to $CF_3CClFCF_3$, and the conversion of a mixture comprising $CF_3CF_2CHCl_2$ and $CClF_2CF_2CHClF$ to a mixture of $CF_3CF_2CHClF$ and $CF_3CF_2CHF_2$.

Examples of unsaturated compounds of the formula $C_pH_e$-$Br_fCl_gF_h$ and $C_rH_j$ which may be reacted with HF in the presence of the catalysts of this invention include $C_2Cl_4$, $C_2BrCl_3$, $C_2Cl_3F$, $C_2Cl_2F_2$, $C_2ClF_3$, $C_2F_4$, $C_2HCl_3$, $C_2HBrCl_2$, $C_2HCl_2F$, $C_2HClF_2$, $C_2HF_3$, $C_2H_2Cl_2$, $C_2H_2ClF$, $C_2H_2F_2$, $C_2H_3Cl$, $C_2H_3F$, $C_2H_4$, $C_3H_6$, $C_3H_5Cl$, $C_3H_4Cl_2$, $C_3H_3Cl_3$, $C_3H_2Cl_4$, $C_3HCl_5$, $C_3Cl_6$, $C_3Cl_5F$, $C_3Cl_4F_2$, $C_3Cl_3F_3$, $C_3Cl_2F_4$, $C_3ClF_5$, $C_3HF_5$, $C_3H_2F_4$, $C_3F_6$, $C_4Cl_8$, $C_4Cl_2F_6$, $C_4ClF_7$, $C_4H_2F_6$, and $C_4HClF_6$.

Specific examples of fluorination reactions of unsaturated halogenated hydrocarbon compounds which may be carried out using the catalysts of this invention include the conversion of $CHCl=CCl_2$ to a mixture of $CH_2ClCF_3$ and $CH_2FCF_3$, the conversion of $CCl_2=CCl_2$ to a mixture of $CHCl_2CF_3$, $CHClFCF_3$, and $CHF_2CF_3$, the conversion of $CCl_2=CH_2$ to a mixture of $CH_3CCl_2F$, $CH_3CClF_2$, and $CH_3CF_3$, the conversion of $CH_2=CHCl$ to a mixture of $CH_3CHClF$ and $CH_3CHF_2$, the conversion of $CF_2=CH_2$ to $CH_3CF_3$, the conversion of $CCl_2=CClCF_3$ to a mixture of $CF_3CCl=CF_2$ and $CF_3CHClCF_3$, the conversion of $CF_3CF=CF_2$ to $CF_3CHFCF_3$, the conversion of $CF_3CH=CF_2$ to $CF_3CH_2CF_3$, and the conversion of $CF_3CH=CHF$ to $CF_3CH_2CHF_2$.

Also of note is a catalytic process for producing a mixture of 2-chloro-1,1,3,3,3-pentafluoropropene (i.e., $CF_3CCl=CF_2$ or CFC-1215xc) and 2-chloro-1,1,1,3,3,3-hexafluoropropane (i.e., $CF_3CHClCF_3$ or HCFC-226da) by the fluorination of one or more halopropene compounds $CX_3CCl=CClX$, wherein each X is independently selected from the group consisting of F and Cl. Preferred halopropenes of the formula $CX_3CCl=CClX$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). The CFC-1215xc/HCFC-226da mixture is produced by reacting the above unsaturated compound(s) with HF in the vapor phase in the presence of the catalysts of this invention at temperatures from about 240° C. to about 400° C., preferably about 250° C. to about 350° C.

The amount of HF fed to the reactor should be at least a stoichiometric amount based on the number of Cl substituents in the $CX_3CCl=CClX$ starting material(s). In the case of fluorination of CFC-1213xa, the stoichiometric ratio of HF to CFC-1213xa is 3:1 for synthesis of HCFC-226da. Preferred ratios of HF to $CX_3CCl=CClX$ starting material(s) are typically in the range of about twice the stoichiometric ratio to about 30:1. Preferred contact times are from 1 to 60 seconds. In contrast to catalyst compositions comprising chromium oxide in the absence of zinc, the catalyst compositions of this invention provide mixtures of CFC-1215xc and HCFC-226da.

Further information on the fluorination of CFC-1213xa to a mixture of CFC-1215xc and HCFC-226da is provided in U.S. patent application 60/511,354 [CL2372 US PRV] filed Oct 14, 2003, and hereby incorporated by reference herein in its entirety (see also corresponding International Application No. PCT/US2004/034455.

Mixtures of saturated halogenated hydrocarbon compounds or mixtures of unsaturated hydrocarbons and/or halogenated hydrocarbon compounds may also be used in the vapor phase fluorination reactions as well as mixtures comprising both unsaturated hydrocarbons and halogenated hydrocarbon compounds. Specific examples of mixtures of saturated halogenated hydrocarbon compounds and mixtures of unsaturated hydrocarbons and unsaturated halogenated hydrocarbon compounds that may be subjected to vapor phase fluorination using the catalysts of this invention include a mixture of $CH_2Cl_2$ and $CCl_2=CCl_2$, a mixture of $CCl_2FCClF_2$ and $CCl_3CF_3$, a mixture of $CCl_2=CCl_2$ and $CCl_2=CClCCl_3$, a mixture of $CH_2=CHCH_3$ and $CH_2=CClCH_3$, a mixture of $CH_2Cl_2$ and $CH_3CCl_3$, a mixture of $CHF_2CClF_2$ and $CHClFCF_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHCl_2CH_2CCl_3$ and $CCl_3CH_2CCl_3$, a mixture of $CF_3CH_2CCl_2F$ and $CF_3CH=CCl_2$, and a mixture of $CF_3CH=CHCl$ and $CF_3CH=CCl_2$.

Where chlorine ($Cl_2$) is present as in chlorofluorinations, the amount of chlorine fed to the reactor is based on whether the halogenated hydrocarbon compounds fed to the reactor is unsaturated and the number of hydrogens in $C_nH_aBr_bCl_cF_d$, $C_qH_r$, $C_pH_eBr_fCl_gF_h$, and $C_rH_j$ that are to be replaced by chlorine and fluorine. One mole of $Cl_2$ is required to saturate a carbon-carbon double bond and a mole of $Cl_2$ is required for each hydrogen to be replaced by chlorine or fluorine. A slight excess of chlorine over the stoichiometric amount may be necessary for practical reasons, but large excesses of chlorine will result in complete chlorofluorination of the products. The ratio of $Cl_2$ to halogenated carbon compound is typically from about 1:1 to about 10:1.

Specific examples of vapor phase chlorofluorination reactions of saturated halogenated hydrocarbon compounds of the general formula $C_nH_aBr_bCl_cF_d$ and saturated hydrocarbon compounds of the general formula $C_qH_r$ which may be carried out using the catalysts of this invention include the conversion of $C_2H_6$ to a mixture containing $CH_2ClCF_3$, the conversion of $CH_2ClCF_3$ to a mixture of $CHClFCF_3$ and $CHF_2CF_3$, the conversion of $CCl_3CH_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CHCl_2$ to a mixture of $CF_3CCl_2CClF_2$, $CF_3CCl_2CF_3$, $CF_3CClFCClF_2$, and $CF_3CClFCF_3$, the conversion of $CCl_3CHClCH_2Cl$ to a mixture of $CF_3CCl_2CClF_2$, $CF_3CCl_2CF_3$, $CF_3CClFCClF_2$, and $CF_3CClFCF_3$, the conversion of $CHCl_2CCl_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CH_2Cl$ to a mixture of $CF_3CCl_2CHF_2$, $CF_3CClFCHF_2$, $CF_3CClFCClF_2$, and $CF_3CCl_2CF_3$, and the conversion of $CCl_3CH_2CHCl_2$ to a mixture of $CF_3CCl_2CHF_2$, $CF_3CClFCHF_2$, $CF_3CClFCClF_2$, and $CF_3CCl_2CF_3$.

Specific examples of vapor phase chlorofluorination reactions of unsaturated halogenated hydrocarbon compounds of the general formula $C_pH_eBr_fCl_gF_h$ and unsaturated hydrocarbon compounds of the general formula $C_rH_j$ which may be carried out using the catalysts of this invention include the conversion of $C_2H_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, the conversion of $C_2Cl_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, and the conversion of $C_3H_6$ or $CF_3CCl=CCl_2$ to a mixture of $CF_3CCl_2CClF_2$, $CF_3CCl_2CF_3$, $CF_3CClFCClF_2$, and $CF_3CClFCF_3$.

Of note is a catalytic process for producing a mixture of 1,2,2-trichloro-1,1,3,3,3-pentafluoropropane (i.e., $CClF_2CCl_2CF_3$ or CFC-215aa) and 1,1,2-trichloro-1,2,3,3,3-pentafluoropropane (i.e., $CF_3CClFCCl_2F$ or CFC-215bb), by the chlorofluorination of a halopropene of the formula $CX_3CCl=CClX$, wherein each X is independently selected from the group F and Cl. Preferred halopropenes of the formula $CX_3CCl=CClX$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). The mixture of CFC-215aa and CFC-215bb is produced by reacting the above unsaturated compounds with $Cl_2$ and HF in the vapor phase in the presence of the catalysts of this invention at temperatures from about 200° C. to about 400° C., preferably about 250° C. to 350° C.

Further information on the chlorofluorination of CFC-1213xa to produce CFC-215aa and CFC-215bb is provided in U.S. patent application Ser. No. 60/511,284 [CL2320 US PRV]filed Oct 14, 2003, and hereby incorporated by reference herein in its entirety (see also corresponding International Application No. PCT/US2004/034454).

Also of note is a catalytic process for producing a mixture of 2,2-dichloro-1,1,1,3,3,3-hexafluoropropane (i.e., $CF_3CCl_2CF_3$ or CFC-216aa) and 1,2-dichloro-1,1,2,3,3,3-hexafluoropropane (i.e., $CF_3CClFCClF_2$ or CFC-216ba), by the chlorofluorination of a halopropene of the formula $CX_3CCl=CX_2$, wherein each X is independently selected from the group F and Cl. Preferred halopropenes of the formula $CX_3CCl=CClX$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). The mixture of CFC-216aa and CFC-216ba is produced by reacting the above unsaturated compounds with $Cl_2$ and HF in the vapor phase in the presence of the catalysts of this invention at temperatures from about 230° C. to about 425° C., preferably about 250° C. to 400° C.

Further information on the chlorofluorination of CFC-1213xa to produce CFC-216aa and CFC-216ba is provided in U.S. patent application Ser. No. 60/511,355 [CL2246 US PRV]filed Oct. 14, 2003, and hereby incorporated by reference herein in its entirety (see also corresponding International Application No. PCT/US2004/034447).

Mixtures of saturated hydrocarbon compounds and saturated halogenated hydrocarbon compounds and mixtures of unsaturated hydrocarbon compounds and unsaturated halogenated hydrocarbon compounds as well as mixtures comprising both saturated and unsaturated compounds may be chlorofluorinated using the catalysts of the present invention. Specific examples of mixtures of saturated and unsaturated hydrocarbons and halogenated hydrocarbons that may be used include a mixture of $CCl_2=CCl_2$ and $CCl_2=CClCCl_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHF_2CH_2CF_3$ and $CHCl=CHCF_3$, and a mixture of $CH_2=CH_2$ and $CH_2=CHCH_3$.

Included in the present invention are embodiments in which the fluorine distribution of a halogenated hydrocarbon compound is changed by rearranging the H, Br, Cl, and F substituents in the molecule (typically to a thermodynamically preferred arrangement) while maintaining the same number of the H, Br, Cl, and F substituents, respectively. This process is referred to herein as isomerization.

In another embodiment of the present invention, the fluorine distribution of a halogenated hydrocarbon compound is changed by exchanging at least one F substituent of one molecule of the halogenated hydrocarbon starting material with at least one H, Br and/or Cl substituent of another molecule of the halogenated hydrocarbon starting material so as to result in the formation of one or more halogenated hydrocarbon compounds having a decreased fluorine content compared to the halogenated hydrocarbon starting material and one or more halogenated hydrocarbon compounds having an increased fluorine content compared to the halogenated hydrocarbon starting material. This process is referred to herein as disproportionation.

In another embodiment of the present invention, both isomerization and disproportionation reactions may occur simultaneously.

Whether carrying out isomerization, disproportionation or both isomerization and disproportionation, the fluorine distribution of saturated compounds of the formula $C_aH_bBr_b$-$Cl_cF_d$ and/or unsaturated compounds of the formula $C_pH_eBr_f$-$Cl_gF_h$ may be changed in the presence of a catalyst composition of this invention.

The isomerization and disproportionation reactions are typically conducted at temperatures of from about 150° C. to 500° C., preferably from about 200° C. to about 400° C. The contact time in the reactor is typically from about 1 to about 120 seconds and preferably from about 5 to about 60 seconds. The isomerization and disproportionation reactions may be carried out in the presence of an inert gas such as helium, argon, or nitrogen. The isomerization and disproportionation reactions may be carried out in the presence of HF and HCl.

Specific examples of vapor phase isomerization reactions which may be carried out using the catalysts of this invention include the conversion of $CClF_2CCl_2F$ to $CCl_3CF_3$, the conversion of $CClF_2CClF_2$ to $CF_3CCl_2F$, the conversion of $CHF_2CClF_2$ to $CF_3CHClF$, the conversion of $CHF_2CHF_2$ to $CF_3CH_2F$, the conversion of $CF_3CClFCClF_2$ to $CF_3CCl_2CF_3$, and the conversion of $CF_3CHFCHF_2$ to $CF_3CH_2CF_3$.

Specific examples of vapor phase disproportionation reactions which may be carried out using the catalysts of this invention include the conversion of $CClF_2CClF_2$ to a mixture of $CClF_2CCl_2F$, $CCl_3CF_3$, and $CF_3CClF_2$, and the conversion of $CHClFCF_3$ to a mixture of $CHCl_2CF_3$, and $CHF_2CF_3$.

Of note is a process for the conversion of a mixture of 2-chloro-1,1,2,2-tetrafluoroethane (i.e., $CHF_2CClF_2$ or HCFC-124a) and 2-chloro-1,1,1,2-tetrafluoroethane (i.e., $CF_3CHClF$ or HCFC-124) to a mixture comprising 2,2-dichloro-1,1,1-trifluoroethane (i.e., $CHCl_2CF_3$ or HCFC-123) and 1,1,1,2,2-pentafluoroethane (i.e., $CF_3CHF_2$ or HFC-125) in addition to unconverted starting materials. The mixture comprising HFC-125 and HCFC-123 may be obtained in the vapor phase by contacting a mixture of HCFC-124a and HCFC-124 over the catalysts of this invention optionally in the presence of a diluent selected from the group consisting of HF, HCl, nitrogen, helium, argon, and carbon dioxide. The disproportionation is preferably conducted at about 150° C. to about 400° C., more preferably about 250° C. to about 350° C. If used, the diluent gas may be present in a molar ratio of diluent to haloethane of from about 1:1 to about 5:1. Preferred contact times are from about 10 seconds to about 60 seconds.

Included in this invention is a process for decreasing the fluorine content of a halogenated hydrocarbon compound by dehydrofluorinating said halogenated hydrocarbon compound in the presence of the catalyst of this invention. Halogenated hydrocarbon compounds suitable as starting materials for the dehydrofluorination processes of this invention include those of the general formula $C_nH_aF_d$, wherein n is an integer from 2 to 6, a is an integer from 1 to 12, d is an integer from 1 to 13, and the sum of a and d is equal to 2n+2.

The dehydrofluorination reactions are typically conducted at temperatures of from about 200° C. to about 500° C., preferably from about 300° C. to about 450° C. The contact time in the reactor is typically from about 1 to about 360 seconds and preferably from about 5 to about 120 seconds. The dehydrofluorination reactions can also be carried out in the presence of an inert gas such as helium, argon, or nitrogen to increase the extent of dehydrofluorination of the halogenated hydrocarbon compound.

The product of dehydrofluorination reaction consists of HF and the unsaturated fluorinated carbon compound resulting from loss of HF from the starting material. Specific examples of vapor phase dehydrofluorination reactions which may be carried out using the catalysts of this invention include the conversion of $CH_3CHF_2$ to $CH_2=CHF$, the conversion of $CH_3CF_3$ to $CH_2=CF_2$, the conversion of $CF_3CH_2F$ to $CF_2=CHF$, the conversion of $CHF_2CH_2CF_3$ to $CHF=CHCF_3$, and the conversion of $CF_3CH_2CF_3$ to $CF_3CH=CF_2$.

Of note is a catalytic process for producing fluoroethene (i.e., $CH_2=CHF$ or vinyl fluoride) by the dehydrofluorination of a 1,1-difluoroethane (i.e., $CHF_2CH_3$ or HFC-152a). A mixture comprising vinyl fluoride and unconverted HFC-152a may be obtained in the vapor phase by contacting HFC-152a over the catalysts of this invention optionally in the presence of a diluent selected from the group consisting of HF, nitrogen, helium, argon, and carbon dioxide. The dehydrofluorination is preferably conducted at about 150° C. to about 400° C., more preferably about 250° C. to about 350° C. If used, the diluent gas may be present in a molar ratio of diluent to haloethane of from about 1:1 to about 5:1. Preferred contact times are from about 10 seconds to about 60 seconds.

Also of note is a catalytic process for producing 1,1,3,3,3-pentafluoropropene (i.e., $CF_2=CHCF_3$ or HFC-1225zc) by the dehydrofluorination of 1,1,1,3,3,3-hexafluoropropane (i.e., $CF_3CH_2CF_3$ or HFC-236fa). A mixture comprising HFC-1225zc and unconverted HFC-236fa may be obtained in the vapor phase by contacting HFC-236fa over the catalysts of this invention optionally in the presence of a diluent selected from the group consisting of HF, nitrogen, helium, argon, and carbon dioxide. The dehydrofluorination is preferably conducted at about 250° C. to about 450° C., more preferably about 300° C. to about 400° C. If used, the diluent gas may be present in a molar ratio of diluent to haloethane of from about 1:1 to about 5:1. Preferred contact times are from about 10 seconds to about 60 seconds.

Included in this invention is a process for decreasing the fluorine content of a halogenated hydrocarbon compound by reacting said halogenated hydrocarbon compound with hydrogen chloride (HCl) in the vapor phase in the presence of a catalyst composition of this invention. Such a process is referred to herein as a chlorodefluorination. Chlorodefluorination is disclosed in U.S. Pat. No. 5,345,017 and U.S. Pat. No. 5,763,698, which two patents are hereby incorporated herein by reference.

Halogenated hydrocarbon compounds suitable as starting materials for the chlorodefluorination processes of this invention may be saturated or unsaturated. Saturated halogenated hydrocarbon compounds suitable for the chlorodefluorination processes of this invention include those of the general formula $C_nH_aCl_cF_d$, wherein n is an integer from 1 to 6, a is an integer from 0 to 12, c is an integer from 0 to 13, d is an integer from 1 to 13, and the sum of a, c and d is equal to 2n+2. Unsaturated halogenated hydrocarbon compounds suitable for the chlorodefluorination processes of this invention include those of the general formula $C_pH_eCl_gF_h$, wherein p is an integer from 2 to 6, e is an integer from 0 to 10, g is an integer from 0 to 12, h is an integer from 1 to 11, and the sum of e, g, and h is equal to 2p. The fluorine content of saturated compounds of the formula $C_nH_aCl_cF_d$ and/or unsaturated compounds of the formula $C_pH_eCl_gF_h$ may be decreased by reacting said compounds with HCl in the vapor phase in the presence of the catalyst compositions of this invention.

The product of chlorodefluorination reactions typically comprise unreacted HCl, HF, unconverted starting material, saturated halogenated hydrocarbon compounds having a lower fluorine content than the starting material and unsaturated halogenated compounds. Specific examples of vapor phase chlorodefluorination reactions which may be carried out using the catalysts of this invention include the conversion of $CHF_3$ to a mixture of $CHCl_3$, $CHCl_2F$, and $CHClF_2$, the conversion of $CClF_2CClF_2$ to a mixture of $CCl_3CCl_3$, $CCl_3CCl_2F$, $CCl_3CClF_2$, $CCl_2FCCl_2F$, $CClF_2CCl_2F$, and $CCl_3CF_3$, the conversion of $CF_3CClF_2$ to a mixture of $CCl_3CCl_3$, $CCl_3CCl_2F$, $CCl_3CClF_2$, $CCl_2FCCl_2F$, $CClF_2CCl_2F$, $CCl_3CF_3$, $CClF_2CClF_2$, and $CF_3CCl_2F$, the conversion of $CF_3CCl_2CF_3$ to a mixture of $CF_3CCl_2CClF_2$, $CF_3CCl_2CCl_2F$, $CF_3CCl_2CCl_3$, and $CClF_2CCl_2CCl_3$, and the conversion of $CF_3CH_2CF_3$ to a mixture of $CCl_2=CHCF_3$, and $CCl_2=CClCF_3$.

The reaction products obtained by the processes of this invention can be separated by conventional techniques, such as with combinations including, but not limited to, scrubbing, decantation, or distillation. Some of the products of the various embodiments of this invention may form one or more azeotropes with each other or with HF.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The processes of this invention can be carried out readily using well known chemical engineering practices.

Utility

Several of the reaction products obtained through use of the catalysts disclosed herein will have desired properties for direct commercial use. For example, $CH_2F_2$ (HFC-32), $CHF_2CF_3$ (HFC-125), $CHF_2CF_3$ (HFC-125), $CH_2FCHF_2$ (HFC-134), $CF_3CH_2CF_3$ (HFC-236fa), and $CF_3CH_2CHF_2$ (HFC-245fa) find application as refrigerants, $CH_2FCF_3$ (HFC-134a) and $CF_3CHFCF_3$ (HFC-227ea) find application as propellants, $CH_2FCHF_2$ (HFC-134) and $CF_3CH_2CHF_2$ (HFC-245fa) find application as blowing agents, and $CHF_2CF_3$ (HFC-125), $CF_3CH_2CF_3$ (HFC-236fa), and $CF_3CHFCF_3$ (HFC-227ea) find application as fire extinguishants.

Other reaction products obtained through the use of this invention are used as chemical intermediates to make useful products. For example, $CCl_3CF_3$ (CFC-113a) can be used to prepare CFC-114a which can then be converted to $CH_2FCF_3$ (HFC-134a) by hydrodechlorination. Similarly, $CF_3CCl_2CF_3$ (CFC-216aa) and $CF_3CHClCF_3$ (HCFC-226da) can be used to prepare $CF_3CH_2CF_3$ (HFC-236fa) by hydrodechlorination. Also, $CF_3CCl=CF_2$ (CFC-1215xc) and $CF_3CCl_2CClF_2$ (CFC-215aa) can be used to prepare $CF_3CH_2CHF_2$ (HFC- 245fa) by hydrogenation and $CF_3CClFCClF_2$ (CFC-216ba) can be used to prepare $CF_3CF=CF_2$ (HFP).

The following specific embodiments are to be construed as merely illustrative, and do not constrain the remainder of the disclosure in any way whatsoever.

EXAMPLES

| LEGEND | |
|---|---|
| CFC-113 is $CClF_2CCl_2F$ | CFC-114 is $CClF_2CClF_2$ |
| CFC-114a is $CF_3CCl_2F$ | HCFC-124 is $CF_3CHClF$ |
| HCFC-124a is $CClF_2CHF_2$ | HFC-125 is $CF_3CHF_2$ |
| CFC-133a is $CF_3CH_2Cl$ | 226da is $CF_3CHClCF_3$ |
| 227ea is $CF_3CHFCF_3$ | 236fa is $CF_3CH_2CF_3$ |
| HCC-1110 is $CCl_2=CCl_2$ | CFC-1111 is $CClF=CCl_2$ |
| HCC-1120 is $CHCl=CCl_2$ | HCFC-1121 is $CHCl=CClF$ |
| 1215xc is $CF_3CCl=CF_2$ | 1225zc is $CF_3CH=CF_2$ |

Catalyst Characterization

Energy Dispersive Spectroscopy (EDS) and Transmission Electron Microscopy (TEM)

In these studies, the crystallites were analyzed using a Philips CM-20 high-resolution transmission electron microscope operated at an accelerating voltage of 200 kV and configured with an Oxford windowless EDS system with a Si(Li) elemental detector. In the EDS analyses, electron-transparent thin sections of samples were used to minimize sample thickness effects such as fluorescence. Also, due to the similarity of their atomic masses, the X-ray absorption cross-sections for Cr and Zn were assumed to be the same (see the discussion by Zaluzec on pages 121 to 167 in *Introduction to Analytical Electron Microscopy* edited by J. J. Hren, J. I. Goldstein, and D. C. Joy (Plenum Press, New York, 1979). The presence of copper in the EDS is due to the TEM grid and background in the microscope.

X-ray Powder Diffraction (XRD)

X-ray diffraction measurements were collected with a Philips XPERT automated powder diffractometer, Model 3040, using CuK(alpha) radiation ($\lambda=1.5406$ Å). These measurements involved a scan between 2-90° 2-theta, with a step of 0.03° and a count time of 2 seconds. The volume dimensions and weight percents were determined using GSAS software and the Rietveld method. The volume average crystallite sizes were estimated using the Materials Data Jade software.

Catalyst Preparation

Preparation Example 1

Preparation of 95% Chromium/5% Zinc Catalyst
(450° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 450° C. for 20 hours, the resulting solid weighed 76.72 g.

Preparation Example 2

Preparation of 90% Chromium/10% Zinc Catalyst
(900° C.)

A solution of 360.13 g $Cr(NO_3)_3[9(H_2O)]$ (0.900 mole) and 29.75 g $Zn(NO_3)_2[6(H_2O)]$ (0.100 mole) was prepared in 1000 mL of deionized water. The solution was treated with 450 mL of 7.4M aqueous ammonium hydroxide over the course of 1.4 hours; the pH increased from 1.9 to pH 8.4. The slurry was stirred at room temperature overnight and then dried at 120° C. in the presence of air. The dried solid was then calcined in air at 900° C. for 20 hours; the resulting solid weighed 75.42 g.

X-ray powder analysis of the sample indicated the presence of three phases: the silicon internal standard, $Cr_2O_3$ (eskolaite), and $ZnCr_2O_4$ (zinc chromite). The weight % $ZnCr_2O_4$ was determined to be 23.9%. There was no significant change in the cell volume of the Cr/Zn sample (0.2896 $nm^3$) in comparison with a 900° C.-calcined $Cr_2O_3$ sample which had been precipitated in the absence of zinc (0.2895 $nm^3$). This indicates that zinc had not been substituted into the $Cr_2O_3$ lattice. The estimated coherent domain size of the $Cr_2O_3$ and $ZnCr_2O_4$ phases was 814 angstroms and 712 angstroms, respectively.

Analysis of the sample by TEM and EDS indicated the presence of chromium oxide phases containing zinc having a Cr/Zn ratio of 2 and a chromium oxide phase containing no zinc.

Preparation Example 3

Preparation of 95% Chromium/5% Zinc Catalyst
(900° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 900C for 20 hours; the resulting solid weighed 70.06 g.

X-ray powder analysis of the sample indicated the presence of three phases: the silicon internal standard, $Cr_2O_3$ (eskolaite), and $ZnCr_2O_4$ (zinc chromite). The weight % $ZnCr_2O_4$ was determined to be 12.1%. There was no significant change in the cell volume of the Cr/Zn sample (0.2894 $nm^3$) in comparison with a 900° C.-calcined $Cr_2O_3$ sample which had been precipitated in the absence of zinc (0.2895 $nm^3$). This indicates that zinc had not been substituted into the $Cr_2O_3$ lattice. The estimated coherent domain size of the $Cr_2O_3$ and $ZnCr_2O_4$ phases was 962 angstroms and 913 angstroms, respectively.

Analysis of the sample by TEM and EDS indicated the presence of chromium oxide phases containing zinc having a Cr/Zn ratio of 2 and a chromium oxide phase containing no zinc.

Preparation Example 4

Preparation of 80% Chromium/20% Zinc Catalyst
(900° C.)

A solution of 320.12 g of $Cr(NO_3)_3[9(H_2O)]$ (0.800 mole) and 59.49 g $Zn(NO_3)_2[6(H_2O)]$ (0.200 mole) was prepared in 1000 mL of deionized water. The solution was treated with 450 mL of 7.4M aqueous ammonium hydroxide over the course of one hour; the pH increased from about 1.7 to about pH 8.4. The slurry was stirred at room temperature overnight and then dried at 120° C. in an oven in the presence of air. The dried solid was then calcined in air at 900° C. for 22 hours; the resulting solid weighed 75.80 g.

X-ray powder analysis of the sample indicated the presence of three phases: the silicon internal standard, $Cr_2O_3$ (eskolaite), and $ZnCr_2O_4$ (zinc chromite). The weight % $ZnCr_2O_4$ was determined to be 60.9%. There was no significant change in the cell volume of the Cr/Zn sample (0.2896 $nm^3$) in comparison with a 900° C.-calcined $Cr_2O_3$ sample which had been precipitated in the absence of zinc (0.2895 $nm^3$). This indicates that zinc had not been substituted into the $Cr_2O_3$ lattice. The estimated coherent domain size of the $Cr_2O_3$ and $ZnCr_2O_4$ phases was 779 angstroms and 679 angstroms, respectively.

Analysis of the sample by TEM and EDS indicated the presence of chromium oxide phases containing zinc having a Cr/Zn ratio of 2 and a chromium oxide phase containing no zinc.

Preparation Example 5

Preparation of 98.1% Chromium/1.9% Zinc Catalyst (550° C.)

A solution of 516.46 g $Cr(NO_3)_3[9(H_2O)]$ (1.29 moles) and 7.31 g $Zn(NO_3)_2[6(H_2O)]$ (0.0246 mole) was prepared in 500 mL of distilled water in 1 L beaker resting on a hot plate. The mixture was then transferred to a Pyrex™ container and the container placed in a furnace. The container was heated from room temperature to 125° C. at 10° C./min and then held at 125° C. for six hours. The container was heated from 125° C. to 350° C. at 1° C./min and then held at 350° C. for six hours. The container was heated from 350° C. to 550° C. at 1° C./min and then held at 550° C. for 24 hours.

Example 1

$CF_3CH_2CF_3$ Dehydrofluorination

A sample of the catalyst prepared in PREPARATION EXAMPLE 5, was pelletized (−12 to +20 mesh, (1.68 to 0.84 mm)); 29.86 g (20 mL) and sieved, and placed in a ⅝" (1.58 cm) diameter Inconel™ nickel alloy reactor tube heated in a fluidized sand bath. The catalyst was purged with nitrogen at about 250° C. prior to use. In addition, the catalyst, which had been previously used in chlorofluorination reactions, was originally fluorinated using a 1:1 ratio of HF and nitrogen (50 cc/min (8.3(10)$^{-7}$ $m^3$/sec) each) at 175° C. The catalyst was then treated with a 4:1 ratio of HF and nitrogen (nitrogen flow rate: 20 cc/min (3.3(10)$^{-7}$ $m^3$/sec); HF flow rate: 80 cc/min (1.3(10)$^{-6}$ $m^3$/sec) as the reactor temperature was gradually increased from 175° C. to 400° C. over several hours. HFC-236fa and nitrogen were fed to the reactor in a 1:4 molar ratio with a catalyst contact time of 15 seconds at a nominal pressure of one atmosphere. The GC-MS analyses of the reactor effluent at 300° C. and 400° C. are given below.

| Component | Mole % | |
|---|---|---|
| | 300° C. | 400° C. |
| HFC-236fa | 92.3 | 59.7 |
| HFC-1225zc | 6.8 | 36.2 |
| HFC-227ea | 0.6 | 3.1 |

Minor products included $CH_3CF_3$, $C_3F_8$, $C_4HF_7$, $CF_3CHClCF_3$, and $C_3HClF_4$ Example 2

Dehydrofluorination of a $CF_3CHClCF_3/CF_3CH_2CF_3$ Mixture

A sample of the catalyst prepared in PREPARATION EXAMPLE 2 was pelletized (−12 to +20 mesh, (1.68 to 0.84 mm)); 26.64 g (15 mL) and sieved and placed in a ⅝" (1.58 cm) diameter Inconel™ nickel alloy reactor tube heated in a fluidized sand bath. The catalyst was purged with nitrogen at about 250° C. prior to use. In addition, the catalyst, which had been previously used in chlorofluorination reactions, was originally fluorinated following a procedure similar to that in EXAMPLE 1. Nitrogen and a mixture comprising HCFC-226da (73.9%), HFC-236fa (25.5%), HFC-1225zc (0.2%), and CFC-216aa (0.1%) were co-fed to the reactor with catalyst contact time of 30 seconds at a nominal pressure of one atmosphere. The molar ratio of nitrogen to fluoropropane mixture was 4:1. The GC-MS analyses of the reactor effluent at 300° C. and 400° C. are given below.

| Component | GC Area % | |
|---|---|---|
| | 300° C. | 400° C. |
| HCFC-226da | 73.2 | 51.4 |
| HFC-236fa | 24.7 | 15.3 |
| HFC-1225zc | 1.5 | 11.3 |
| CFC-1215xc | 0.2 | 17.0 |

Minor products included $CH_3CF_3$, $C_3H_3F_3$, $C_3H_2F_4$, $CF_3CF=CHF$, $CF_3CHClCF_3$, $C_3HClF_4$, $C_3Cl_2F_6$, and $C_3Cl_2F_4$.

Example 3

Disproportionation of a $CF_3CHClF/CClF_2CHF_2$ Mixture Nitrogen and a mixture comprising HCFC-124a (97.1 mole %), HCFC-124 (2.4 mole %), and CFC-114 (0.4 mole %) were co-fed to the reactor containing the catalyst used in EXAMPLE 2. The molar ratio of nitrogen to the 124/124a mixture was 2:1 and the contact time was 30 seconds. The GC-MS analyses of the reactor effluent at 300° C. and 400° C. are given below.

| Component | Mole % | |
|---|---|---|
| | 300° C. | 400° C. |
| HFC-125 | 1.5 | 21.4 |
| HCFC-124 | 2.1 | 3.7 |
| HCFC-124a | 94.9 | 61.9 |

-continued

| Component | Mole % 300° C. | 400° C. |
|---|---|---|
| CFC-133a | — | 2.1 |
| $C_2HCl_2F_3$ isomers | 0.7 | 3.3 |
| HCC-1110 | — | 0.5 |
| HCC-1120 | — | 1.4 |
| CFC-1111 | 0.03 | 2.2 |
| $C_2Cl_2F_2$ isomers | 0.06 | 1.7 |
| HCFC-1121 | 0.02 | 0.7 |
| CFC-114a | — | 2.1 |
| CFC-114 | 0.4 | 0.4 |
| CFC-113 | — | 0.3 |

Minor products included $CF_3CH_2CF_3$, $CF_3CH_2Cl$, $C_3HF_5$, $CF_3CHClCF_3$, $C_2HCl_3F_2$, $C_2Cl_2F_4$, $C_2ClF_5$ and $C_2Cl_2F_2$.

What is claimed is:

1. A chromium-containing catalyst composition, comprising:
   $ZnCr_2O_4$; and
   crystalline α-chromium oxide;
   wherein the $ZnCr_2O_4$ contains between 10 atom percent and 67 atom percent of the chromium in the composition and at least 70 atom percent of the zinc in the composition, and wherein at least 90 atom percent of the chromium present as chromium oxide in the composition is present as $ZnCr_2O_4$ or crystalline α-chromium oxide.

2. The chromium-containing catalyst composition of claim 1 wherein the $ZnCr_2O_4$ contains between 20 atom percent and 50 atom percent of the chromium in the composition.

3. The chromium-containing catalyst composition of claim 1 wherein the $ZnCr_2O_4$ contains at least 90 atom percent of the zinc in the composition.

4. The chromium-containing catalyst composition of claim 1 wherein greater than 95% of the chromium that is not present as zinc chromite is present as crystalline α-chromium oxide.

5. The chromium-containing catalyst composition of claim 1 which consists essentially of $ZnCr_2O_4$ and crystalline α-chromium oxide.

6. A chromium-containing catalyst composition prepared by treatment of the composition of claim 1 with a fluorinating agent.

7. The chromium-containing catalyst composition of claim 6 wherein the fluorinating agent is anhydrous hydrogen fluoride.

8. A process for changing the fluorine distribution in a halogenated hydrocarbon, or incorporating fluorine in a saturated or unsaturated hydrocarbon, in the presence of a catalyst characterized by: using as a catalyst at least one composition selected from the group consisting of (i) the chromium-containing catalyst compositions of claim 1 and (ii) chromium-containing catalyst compositions prepared by treatment of a composition of claim 1 with a fluorinating agent.

9. The process of claim 8 wherein the fluorine content of a halogenated hydrocarbon compound or an unsaturated hydrocarbon compound is increased by reacting said compound with hydrogen fluoride in the vapor phase in the presence of said catalyst composition.

10. The process of claim 8 wherein the fluorine content of a halogenated hydrocarbon compound or a hydrocarbon compound is increased by reacting said compound with HF and $Cl_2$ in the vapor phase in the presence of said catalyst composition.

11. The process of claim 8 wherein the fluorine distribution in a halogenated hydrocarbon compound is changed by isomerizing said halogenated hydrocarbon compound in the presence of said catalyst composition.

12. The process of claim 8 wherein the fluorine distribution in a halogenated hydrocarbon compound is changed by disproportionating said halogenated hydrocarbon compound in the vapor phase in the presence of said catalyst composition.

13. The process of claim 8 wherein the fluorine content of a halogenated hydrocarbon compound is decreased by dehydrofluorinating said halogenated hydrocarbon compound in the presence of said catalyst composition.

14. The process of claim 8 wherein the fluorine content of a halogenated hydrocarbon compound is decreased by reacting said halogenated hydrocarbon compound with hydrogen chloride in the vapor phase in the presence of said catalyst composition.

15. A method for preparing the chromium-containing catalyst composition of claim 1 comprising:
   (a) co-precipitating a solid by adding ammonium hydroxide to an aqueous solution of a soluble zinc salt and a soluble trivalent chromium salt that contains at least three moles of nitrate per mole of obromium in the solution and has a zinc concentration of from 5 mole % to 25 mole % of the total concentration of zinc and chromium in the solution and where at least three moles of ammonium per mole of chromium in the solution has been added to the solution;
   (b) collecting the co-precipitated solid formed in (a);
   (c) drying the collected solid; and
   (d) calcining the dried solid.

16. The process of claim 15 wherein $ZnCr_2O_4$ is formed during (d).

* * * * *